US005681590A

United States Patent [19]
Bechard et al.

[11] Patent Number: 5,681,590
[45] Date of Patent: *Oct. 28, 1997

[54] DRY MIX FORMULATION FOR BISPHOSPHONIC ACIDS

[75] Inventors: Simon R. Bechard, Quebec, Canada; Kenneth A. Kramer, Green Lane; Ashok V. Katdare, Norristown, both of Pa.

[73] Assignee: Merck & Co., Inc., Rahway, N.J.

[*] Notice: The term of this patent shall not extend beyond the expiration date of Pat. No. 5,358,941.

[21] Appl. No.: 454,100

[22] PCT Filed: Nov. 17, 1993

[86] PCT No.: PCT/US93/11172

§ 371 Date: Jul. 26, 1995

§ 102(e) Date: Jul. 26, 1995

[87] PCT Pub. No.: WO94/12200

PCT Pub. Date: Jun. 9, 1994

Related U.S. Application Data

[63] Continuation of Ser. No. 984,399, Dec. 2, 1992, Pat. No. 5,358,941.

[51] Int. Cl.⁶ .................................................. A61K 9/20
[52] U.S. Cl. .................................... 424/464; 424/465
[58] Field of Search .................................... 424/464, 465

[56] References Cited

U.S. PATENT DOCUMENTS

| 4,942,157 | 7/1990 | Gall et al. ........................ 514/108 |
| 5,041,428 | 8/1991 | Isomura et al. ..................... 514/102 |
| 5,047,246 | 9/1991 | Gallian et al. ..................... 424/464 |
| 5,070,108 | 12/1991 | Margolis ............................ 514/725 |
| 5,158,944 | 10/1992 | Makino et al. ..................... 514/167 |

FOREIGN PATENT DOCUMENTS

| 1 036 368 | 7/1966 | United Kingdom . |
| 1036368 | 7/1966 | United Kingdom . |

OTHER PUBLICATIONS

Remington's Pharmaceutical Science, 15th Edition Mack Pub. Co., Easton, Pa. pp. 1586–1588.

*Primary Examiner*—Amy Hulina
*Attorney, Agent, or Firm*—Joanne M. Giesser; Melvin Winokur

[57] ABSTRACT

Pharmaceutical compositions of bisphosphonic acids, and salts thereof, are prepared by direct compression/dry mix tablet formulation. These pharmaceutical compositions are useful in the treatment of disturbances involving calcium or phosphate metabolism, in particular, the treatment and prevention of diseases involving bone resorption, especially osteoporosis, Paget's disease, malignant hypercalcemia, and metastatic bone disease.

17 Claims, No Drawings

5,681,590

DRY MIX FORMULATION FOR BISPHOSPHONIC ACIDS

This application is the U.S. National Phase Application of International patent application Ser. No. PCT/US93/11172, filed Nov. 17, 1993, which is a continuation of U.S. patent application Ser. No. 984,399, filed Dec. 2, 1992, now U.S. Pat. No. 5,358,941, issued Oct. 25, 1994.

BACKGROUND OF THE INVENTION

The pharmaceutical industry employs various methods for compounding pharmaceutical agents in tablet formulations. In particular, wet granulation is one of the most prevalent methods.

A variety of bisphosphonic acids have been disclosed as being useful in the treatment and prevention of diseases involving bone resorption. Representative examples may be found in the following: U.S. Pat. No. 3,962,432; U.S. Pat. No. 4,054,598; U.S. Pat. No. 4,267,108; U.S. Pat. No. 4,327,039; U.S. Pat. No. 4,621,077; U.S. Pat. No. 4,624,947; U.S. Pat. No. 4,746,654; U.S. Pat. No. 4,922,077; and EPO Patent Pub. No. 0,252,504. Standard methods for tablet formulation of bisphosphonic acids, however, suffer serious difficulties.

In particular, bisphosphonic acids which bear a basic nitrogen-containing functionality may interact with the lactose of standard formulations resulting in discoloration, instability and potency loss. This degradation of the active ingredient is particularly pronounced in the presence of water and/or elevated temperature. It is speculated that this incompatibility is specifically due to the Maillard (or "browning") reaction in which the free amino group of the bisphosphonic acid reacts with the "glycosidic" hydroxyl group of a sugar (such as lactose) ultimately resulting in the formation of brown pigmented degradates. Although this problem may be avoided by the elimination of lactose, the use of lactose as an inert diluent is generally desirable.

The present invention solves this problem by providing a tablet formulation and process therefor that avoids such interaction between the bisphosphonic acid and the lactose in the formulation. In addition, the present invention also provides a processing advantage since it requires only blending of the ingredients without granulation or addition of water prior to compression.

DESCRIPTION OF THE INVENTION

The present invention is directed in a first embodiment to a process for the preparation of pharmaceutical compositions of bisphosphonic acids by direct compression (dry mix) tablet formulation. This process employs a blend of a bisphosphonic acid and minimal amounts of other processing aids with no water added. The tablet formulation is prepared by mixing the formulation ingredients with no hydration (i.e. no additional water is added to the mixture) prior to direct compression.

More specifically, this embodiment of the present invention concerns a process for the preparation of a tablet containing a bisphosphonic acid as an active ingredient which process comprises:

forming a mixture by mixing the active ingredient with:
a diluent,
a dry binder,
a disintegrant,
and optionally one or more additional ingredients selected from the group consisting of: compression aids, flavors, flavor enhancers, sweeteners and preservatives; lubricating the mixture with a lubricant; and compressing the resultant lubricated mixture into a desired tablet form.

The disclosed process may be used to prepare solid dosage forms, particularly tablets, for medicinal administration.

Preferred diluents include lactose. In particular, anydrous lactose is preferred from the flow processing point of view, although hydrous fast flow lactose may also be employed.

A preferred dry binder is cellulose. In particular, microcrystalline cellulose is preferred. Microcrystalline cellulose is available commercially under the trade name "Avicel" from FMC Corporation.

The disintegrant may be one of several modified starches or modified cellulose polymers, in particular, crosscarmellose sodium is preferred. Crosscarmellose sodium NF Type A is commercially available under the trade name "Ac-di-sol".

Preferred lubricants include magnesium stearate.

Examples of the bisphosphonic acids which may be employed as active ingredients in the instant invention include:

4-amino-1-hydroxybutylidene-1,1-bisphosphonic acid;

N-methyl-4-amino-1-hydroxybutylidene-1,1-bisphosphonic acid;

4-(N,N-dimethylamino)-1-hydroxybutylidene-1,1-bisphosphonic acid;

3-amino-1-hydroxypropylidene-1,1-bisphosphonic acid;

3-(N,N-dimethylamino)-1-hydroxypropylidene-1,1-bisphosphonic acid;

1-hydroxy-3-(N-methyl-N-pentylamino)propylidene-1,1-bisphosphonic acid;

1-hydroxy-2-[3-pyridyl]ethylidene-1,1-bisphosphonic acid; and 4-(hydroxymethylene-1,1-bisphosphonic acid)piperidine;

or a pharmaceutically acceptable salt thereof.

Methods for the preparation of bisphosphonic acids may be found in, e.g., U.S. Pat. No. 3,962,432; U.S. Pat. No. 4,054,598; U.S. Pat. No. 4,267,108; U.S. Pat. No. 4,327,039; U.S. Pat. No. 4,407,761; U.S. Pat. No. 4,621,077; U.S. Pat. No. 4,624,947; U.S. Pat. No. 4,746,654; U.S. Pat. No. 4,922,077; and EPO Patent Pub. No. 0,252,504. In particular, methods for the preparation of 4-amino-1-hydroxy-butylidene-1,1-bisphosphonic acid and 4-amino-1-hydroxy-butylidene-1,1-bisphosphonic acid monosodium salt trihydrate may be found in U.S. Pat. No. 4,407,761 and U..S. Pat. No. 4,922,077, respectively.

The pharmaceutically acceptable salts of bisphosphonic acids may also be employed in the instant invention. Examples of base salts of bisphosphonic acids include ammonium salts, alkali metal salts such as potassium and sodium (including mono-, di- and tri-sodium) salts (which are preferred), alkaline earth metal salts such as calcium and magnesium salts, salts with organic bases such as dicyclohexylamine salts, N-methyl-D-glucamine, and salts with amino acids such as arginine, lysine, and so forth. The non-toxic, physiologically acceptable salts are preferred. The salts may be prepared by methods known in the art, such as in U.S. Pat. No. 4,922,077.

In the present invention it is preferred that the bisphosphonic acid is 4-amino-1-hydroxybutylidene-1,1-bisphosphonic acid. It is even more preferred that the bisphosphonic acid is a sodium salt of 4-amino-1-hydroxybutylidene-1,1-bisphosphonic acid, in particular, 4-amino-1-hydroxybutylidene-1,1-bisphosphonic acid monosodium salt trihydrate.

Another embodiment of the present invention is a direct compression pharmaceutical composition, such as a tablet, comprising a bisphosphonic acid, which is prepared by the disclosed process. In general, these pharmaceutical compositions comprise by weight, about 0.5 to 40% by weight of a bisphosphonic acid as an active ingredient; and from about 60 to 99.5% by weight of processing aids with no water added. More specifically, the processing aids are a diluent, a dry binder, a disintegrant and a lubricant. Preferred processing aids include: anhydrous lactose or hydrous fast flow lactose; microcrystalline cellulose; croscarmallose sodium; and magnesium stearate.

Preferred pharmaceutical compositions comprise about 0.5 to 40% by weight of a bisphosphonic acid as an active ingredient; about 10 to 80% by weight of anhydrous lactose or hydrous fast flow lactose; about 5 to 50% by weight of microcrystalline cellulose; about 0.5 to 10% by weight of croscarmallose sodium; and about 0.1 to 5% by weight of magnesium stearate.

The prefected pharmaceutical compositions are generally in the form of tablets. The tablets may be, for example, from 50 mg to 1.0 g in net weight, more preferably 100 to 500 mg net weight, and even more preferably 200 to 300 mg net weight.

More preferred pharmaceutical compositions in accordance with the present invention comprise: about 0.5 to 25% by weight of a bisphosphonic acid selected from 4-amino-1-hydroxybutylidene-1,1-bisphosphonic acid and 4-amino-1-hydroxybutylidene-1,1-bisphosphonic acid monosodium salt trihydrate; about 30 to 70% by weight of anhydrous lactose or hydrous fast flow lactose; about 30 to 50% by weight of microcrystalline cellulose; about 0.5 to 5% by weight of croscarmallose sodium; and about 0.1 to 2% by weight of magnesium stearate.

Especially preferred pharmaceutical compositions comprise about 1 to 25% of the active ingredient, about 40 to 60% by weight of anhydrous lactose; about 35 to 45% by weight of microcrystalline cellulose; about 0.5 to 2% by weight of croscarmallose sodium; and about 0.1 to 1% by weight of magnesium stearate. Preferred pharmaceutical compositions as envisioned for commercial development are as follows.

Tablets of 2.5 mg potency free acid:
about 1.63% by weight of 4-amino-1-hydroxy-butylidene-1,1-bisphosphonic acid monosodium salt trihydrate; about 56.87% by weight of anhydrous lactose; about 40% by weight of microcrystalline cellulose; about 1% by weight of croscarmailose sodium; and about 0.5% by weight of magnesium stearate.

Tablets of 5 mg potency free acid:
about 3.25% by weight of 4-amino-1-hydroxy-butylidene-1,1-bisphosphonic acid monosodium salt trihydrate; about 55.25% by weight of anhydrous lactose; about 40% by weight of microcrystalline cellulose; about 1% by weight of croscarmallose sodium; and about 0.5% by weight of magnesium stearate.

Tablets of 25 mg potency free acid:
about 16.4% by weight of 4-amino-1-hydroxy-butylidene-1,1-bisphosphonic acid monosodium salt trihydrate; about 42.1% by weight of anhydrous lactose; about 40% by weight of microcrystalline cellulose; about 1% by weight of croscarmallose sodium; and about 0.5% by weight of magnesium stearate.

Tablets of 50 mg potency free acid:
about 21.8% by weight of 4-amino-1-hydroxy-butylidene-1,1-bisphosphonic acid monosodium salt trihydrate; about 36.7% by weight of anhydrous lactose; about 40% by weight of microcrystalline cellulose; about 1% by weight of croscarmallose sodium; and about 0.5% by weight of magnesium stearate.

The pharmaceutical tablet compositions of the present invention may also contain one or more additional formulation ingredients may be selected from a wide variety of excipients known in the pharmaceutical formulation art. According to the desired properties of the tablet, any number of ingredients may be selected, alone or in combination, based upon their known uses in preparing tablet compositions. Such ingredients include, but are not limited to, diluents, compression aids, disintegrants, lubricants, binders, flavors, flavor enhancers, sweetenter and preservatives.

The term "tablet" as used herein is intended to encompass compressed pharmaceutical dosage formulations of all shapes and sizes, whether coated or uncoated. Substances which may be used for coating include hydroxypropylmethylcellulose, hydroxypropylcellulose, titanium oxide, talc, sweeteners, and colorants.

The pharmaceutical compositions of the present invention are useful in the therapeutic or prophylactic treatment of disorders in calcium or phosphate metabolism and associated diseases. These diseases can be divided into two categories:

1. Abnormal (ectopic) depositions of calcium salts, mostly calcium phosphate, pathological hardening of tissues and bone malformations.
2. Conditions which can benefit from a reduction in bone resorption. A reduction in bone resorption should improve the balance between resorption and formation, reduce bone loss or result in bone augmentation. A reduction in bone resorption can aleviate the pain associated with osteolytic lesions and reduce the incidence and/or growth of those lesions.

These diseases include: osteoporosis (including estrogen defficiency, immobilization, glucocorticoid induced and senile), osteodystrophy, Paget's disease, myositis ossificans, Bechterew's disease, malignant hypercalcimia, metastatic bone disease, peridontal disease, cholelithiasis, nephrolithiasis, urolithiasis, urinary calculus, hardening of the arteries (sclerosis), arthritis, bursitis, neuritis and tetany.

Increased bone resorption can be accompanied by pathologically high calcium and phosphate concentrations in the plasma, which would be aleviated by use of the instant pharmaceutical compositons.

The following examples are given for the purpose of illustrating the present invention and shall not be construed as being limitations on the scope or spirit of the invention.

EXAMPLE 1
Procedure for Manufacturing 5 mg Potency Tablets of 4-Amino-1-hydroxybutylidene-1,1-bisphosphonic acid

| Ingredients | Per Tablet | Per 4,000 Tablets |
| --- | --- | --- |
| Active ingredient (monosodium salt trihydrate) | 6.55 mg | 26.2 g |
| Anhydrous Lactose, NF | 110.45 mg | 441.8 g |
| Microcrystaline Cellulose NF | 80.0 mg | 320.0 g |
| Magnesium Stearate Impalpable Powder NF | 1.00 mg | 4.0 g |
| Croscarmellose Sodium NF Type A | 2.00 mg | 8.0 g |

The active ingredient (equivalent to 5 mg anhydrous free acid per tablet) was premixed with ⅓ of the microcrystaline cellulose NF and ½ of the anhydrous lactose NF in a ribbon blender for 5 minutes at 20 RPM. To the premix was added the remaining ⅔ of the microcrystaline cellulose NF and the remaining ½ of the anhydrous lactose NF. This was blended for 10 minutes at 20 RPM. Crosscarmellose sodium was added to the blended powders and mixed for 5 minutes at 20 RPM. Finally the magnesium stearate was added to the mixture by passing through a 90 mesh screen and blended for an additional 5 minutes at 20 RPM. The lubricated mixture was compressed to provide tablets of 5 mg active ingredient.

EXAMPLE 2
Procedure for Manufacturing 2.5 mg Potency Tablets of 4-Amino-1-hydroxybutylidene-1,1-bisphosphonic acid

| Ingredients | Per Tablet |
|---|---|
| Active ingredient (monosodium salt trihydrate) | 3.26 mg |
| Anhydrous Lactose, NF | 113.74 mg |
| Microcrystaline Cellulose NF | 80.0 mg |
| Magnesium Stearate Impalpable Powder NF | 1.00 mg |
| Croscarmellose Sodium NF Type A | 2.00 mg |

Tablets were prepared using the procedure of Example 1.

EXAMPLE 3
Procedure for Manufacturing 10.0 mg Potency Tablets of 4-Amino-1-hydroxybutylidene-1,1-bisphosphonic acid

| Ingredients | Per Tablet |
|---|---|
| Active ingredient (monosodium salt trihydrate) | 13.05 mg |
| Anhydrous Lactose, NF | 103.95 mg |
| Microcrystaline Cellulose NF | 80.0 mg |
| Magnesium Stearate Impalpable Powder NF | 1.00 mg |
| Croscarmellose Sodium NF Type A | 2.00 mg |

Tablest were prepared using the procedure of Example 1.

EXAMPLE 4
Procedure for Manufacturing 40.0 mg Potency Tablets of 4-Amino-1-hydroxybutylidene-1,1-bisphosphonic acid

| Ingredients | Per Tablet |
|---|---|
| Active ingredient (monosodium salt trihydrate) | 51.21 mg |
| Anhydrous Lactose, NF | 64.79 mg |
| Microcrystaline Cellulose NF | 80.0 mg |
| Magnesium Stearate Impalpable Powder NF | 1.00 mg |
| Croscarmellose Sodium NF Type A | 2.00 mg |

Tablets were prepared using the procedure of Example 1.

EXAMPLE 5
Procedure for Manufacturing 25 mg Potency Tablets of 4-Amino-1-hydroxybutylidene-1,1-bisphosphonic acid

| Ingredients | Per Tablet | Per 4,000 Tablets |
|---|---|---|
| Active ingredient (monosodium salt trihydrate) | 32.75 mg | 131.0 g |
| Anhydrous Lactose, NF | 84.25 mg | 337.0 g |
| Microcrystaline Cellulose NF | 80.0 mg | 320.0 g |
| Magnesium Stearate Impalpable Powder NF | 1.00 mg | 4.0 g |
| Croscarmellose Sodium NF Type A | 2.00 mg | 8.0 g |

Tablets were prepared using the procedure of Example 1.

EXAMPLE 6
Procedure for Manufacturing 50 mg Potency Tablets of 4-Amino-1-hydroxybutylidene-1,1-bisphosphonic acid

| Ingredients | Per Tablet | Per 2,500 Tablets |
|---|---|---|
| Active ingredient (monosodium salt trihydrate) | 65.5 mg | 163.75 g |
| Anhydrous Lactose, NF | 110.45 mg | 275.0 g |
| Microcrystaline Cellulose NF | 120.0 mg | 300.0 g |
| Magnesium Stearate Impalpable Powder NF | 1.00 mg | 3.75 g |
| Croscarmellose Sodium NF Type A | 2.00 mg | 7.5 g |

Tablets were prepared using the procedure of Example 1.

EXAMPLE 7

Stability Studies

Tablet formulations of the active ingredient (equivalent to 5 mg anhydrous free 4-amino-1-hydroxy-butylidene-1,1-bisphosphonic acid per tablet) were prepared under different conditions with differing excipients. The direct compression tablets were prepared according to the procedure of Example 1 and the wet granulated tablets were prepared according to the procedure below. The tablets were subjected to stability studies under open dish conditions at 40° C./75% relative humidity. The following observations were noted:

1. Tablet discoloration occured within 2 weeks in formulations which were manufactured by wet granulation and contained anhydrous lactose.

2. Tablet discoloration occured within 4 weeks in formulations which were manufactured by wet granulation and contained hydrous lactose.

3. There was no tablet discoloration after 4 weeks in formulations which manufactured as a direct compression (dry mix) formulation. Assay of the active ingredient confirmed that there was no loss of potency or formation of degradates over the same time period. Table I demonstrates the stability characteristics of the direct compression formulation as compared to a wet granulated formulation.

TABLE I

Three-Month Data of 5 mg Probe Stability Lots

(a). Direct Compression

| | Assay, % initial | | | |
|---|---|---|---|---|
| | Open Dish | | HDPE/CRC Bottle | |
| Condition | cpd | Adduct | MK-0217 | Adduct |
| 40° C. | 101.2% | — | 99.8% | — |
| 40° C./75% RH | 102.9% | — | 98.5% | — |
| | | | 100.9%* | — |
| 60° C. | 100.6% | — | 101.3% | — |
| RT/90% RH | 103.5% | — | 102.1% | — |

(b). Wet Granulation

| | Assay, % initial | | | |
|---|---|---|---|---|
| | Open Dish | | HDPE/CRC Bottle | |
| Condition | cpd | Adduct | MK-0217 | Adduct |
| 40° C. | 99.7% | — | 97.0% | — |
| | | | 100.0%** | — |
| 40° C./75% RH | 84.1% | 15.9% | 94.6% | 5.6% |
| | | | 99.7%** | — |
| 60° C. | 92.6% | trace*** | 94.3% | trace*** |
| | | | 94.6%** | trace |
| RT/90% RH | 101.4% | — | 100.4% | — |
| | | | 99.4% | — |

*Duplicate value
**With desiccant
***Trace indicates that the adduct peak is detectable (~5%) but not quantifiable under experimental conditions.
cpd = 4-amino-1-hydroxybutylidene-1,1-bisphosphonic acid Process for wet granulation tablets 1) Anhydrous lactose, alendronate sodium and microcrystalline cellulose was mixed in a suitable size blender.
2) The blend was strained through mesh #30 followed by remixing for an additional time.
3) The powder mixture was granulated with an adequate quantity of water until caking occurred.
4) The wet mass was poured through a screen #5.
5) The wet sized granulation was dried in a forced air dryer at 40°–50° C. until the loss on drying was less then 2% at 105° C.
6) The dry granulation was sized through a suitable screen.
7) The drysized granulation was mixed with croscarmellose sodium followed by magnesium stearate.
8) Tablets were compressed using the labeled granulation.

While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

What is claimed is:

1. A process for the preparation of a tablet containing an active ingredient selected from:
   4-amino-1-hydroxybutylidene-1,1-bisphosphonic acid;
   N-methyl-4-amino-1-hydroxybutylidene-1,1-bisphosphonic acid;
   4-(N,N-dimethylamino)-1-hydroxybutylidene-1,1-bisphosphonic acid;
   3-amino-1-hydroxypropylidene-1,1-bisphosphonic acid;
   3-(N,N-dimethylamino)-1-hydroxypropylidene-1,1-bisphosphonic acid;
   1-hydroxy-3-(N-methyl-N-pentylamino)propylidene-1,1-bisphosphonic acid;
   1-hydroxy-2-[3-pyridyl]ethylidene-1,1-bisphosphonic acid;
   4-(hydroxymethylene-1,1-bisphosphonic acid)piperidine;
   or a pharmaceutically acceptable salts thereof;
   which process comprises:
   forming a mixture by mixing the active ingredient with:
   a diluent, selected from: anhydrous lactose and hydrous fast
   flow lactose,
   a dry binder,
   a disintegrant,
   and optionally one or more additional ingredients selected
   from the group consisting of: compression aids, flavors, flavor enhancers, sweeteners and preservatives;
   lubricating the mixture with a lubricant; and
   compressing the resultant lubricated mixture into a desired
   tablet form.

2. The process of claim 1 wherein the active ingredient is 4-amino-1-hydroxybutylidene-1,1-bisphosphonic acid.

3. The process of claim 1 wherein the active ingredient is 4-amino-1-hydroxybutylidene-1,1-bisphosphonic acid monosodium salt trihydrate.

4. The process of claim 1 wherein the dry binder is microcrystalline cellulose.

5. The process of claim 1 wherein the disintegrant is selected from the group consisting of modified starch, modified cellulose polymer, and croscarmallose sodium, and a combination thereof.

6. The process of claim 1 wherein the disintegrant is croscarmallose sodium.

7. The process of claim 1 wherein the lubricant is magnesium stearate.

8. A solid dosage form containing an active ingredient selected from the group consisting of:
   4-amino-1-hydroxybutylidene-1,1-bisphosphonic acid;
   N-methyl-4-amino-1-hydroxybutylidene-1,1-bisphosphonic acid;
   4-(N,N-dimethylamino)-1-hydroxybutylidene-1,1-bisphosphonic acid;
   3-amino-1-hydroxypropylidene-1,1-bisphosphonic acid;
   3-(N,N-dimethylamino)-1-hydroxypropylidene-1,1-bisphosphonic acid;
   1-hydroxy-3-(N-methyl-N-pentylamino)propylidene-1,1-bisphosphonic acid;
   1-hydroxy-2-[3-pyridyl]ethylidene-1,1-bisphosphonic acid; and
   4-(hydroxymethylene-1,1-bisphosphonic acid)piperidine;
   or a pharmaceutically acceptable salt thereof;
   wherein the dosage form is prepared by the process of claim 1.

9. A pharmaceutical composition comprising by weight, about 0.5 to 40% by weight of an active ingredient selected from the group consisting of:
   4-amino-1-hydroxybutylidene-1,1-bisphosphonic acid;
   N-methyl-4-amino-1-hydroxybutylidene-1,1-bisphosphonic acid;
   4-(N,N-dimethylamino)-1-hydroxybutylidene-1,1-bisphosphonic acid;
   3-amino-1-hydroxypropylidene-1,1-bisphosphonic acid;
   3-(N,N-dimethylamino)-1-hydroxypropylidene-1,1-bisphosphonic acid;
   1-hydroxy-3-(N-methyl-N-pentylamino)propylidene-1,1-bisphosphonic acid;

1-hydroxy-2-[3-pyridyl]ethylidene-1,1-bisphosphonic acid; and 4-(hydroxymethylene-1,1-bisphosphonic acid)piperidine;

or a pharmaceutically acceptable salt thereof;
and from about 60 to 99.5% by weight of excipients consisting essentially of: hydrous fast flow lactose; microcrystalline cellulose; croscarmallose sodium; and magnesium stearate.

10. A pharmaceutical composition comprising by weight, about 0.5 to 40% by weight of an active ingredient selected from the group consisting of:

4-amino-1-hydroxybutylidene-1,1-bisphosphonic acid;

N-methyl-4-amino-1-hydroxybutylidene-1,1-bisphosphonic acid;

4-(N,N-dimethylamino)-1-hydroxybutylidene-1,1-bisphosphonic acid;

3-amino-1-hydroxypropylidene-1,1-bisphosphonic acid;

3-(N,N-dimethylamino)-1-hydroxypropylidene-1,1-bisphosphonic acid;

1-hydroxy-3-(N-methyl-N-pentylamino)propylidene-1,1-bisphosphonic acid;

1-hydroxy-2-[3-pyridyl]ethylidene-1,1-bisphosphonic acid; and 4-(hydroxymethylene-1,1-bisphosphonic acid)piperidine;

or a pharmaceutically acceptable salt thereof;
about 10 to 80% by weight of hydrous fast flow lactose;
about 5 to 50% by weight of microcrystalline cellulose;
about 0.5 to 10% by weight of croscarmallose sodium; and
about 0.1 to 5% by weight of magnesium stearate.

11. The pharmaceutical composition of claim 10 comprising about 0.5 to 25% by weight of the active ingredient, about 30% to 70% by weight of hydrous fast flow lactose; about 30 to 50% by weight of microcrystalline cellulose; about 0.5 to 5% by weight of croscarmallose sodium; and about 0.1 to 2% by weight of magnesium stearate.

12. The pharmaceutical composition of claim 10 wherein the active ingredient is 4-amino-1-hydroxybutylidene-1,1-bisphosphonic acid.

13. The pharmaceutical composition of claim 10 wherein the active ingredient is 4-amino-1-hydroxybutylidene-1,1-bisphosphonic acid monosodium salt trihydrate.

14. A tablet prepared from the pharmaceutical composition of claim 13.

15. A tablet prepared from the pharmaceutical composition of claim 10.

16. A process for the preparation of a table containing as active ingredient a basic nitrogen containing bisphosphonate: which process comprises:

forming a mixture by mixing the active ingredient with:
a diluent, selected from: anhydrous lactose or hydrous fast flow lactose,
a dry binder,
a disintegrant,
and optionally one or more additional ingredients selected
from the group consisting of: compression aids, flavors, flavor enhancers, sweeteners and preservatives;
lubricating the mixture with a lubricant; and
compressing the resultant lubricated mixture into a desired tablet form.

17. A solid dosage form containing as active ingredient a basic nitrogen containing bisphosphonate wherein the dosage form is prepared by the process of claim 1.

* * * * *